United States Patent [19]

Dickerson et al.

[11] Patent Number: 5,533,988
[45] Date of Patent: Jul. 9, 1996

[54] OVER-THE-NEEDLE CATHETER

[75] Inventors: Charles W. Dickerson, Tustin; Richard A. Overton, Santa Ana; Ronald B. Luther, Newport Beach, all of Calif.

[73] Assignee: Luther Medical Products, Inc., Tustin, Calif.

[21] Appl. No.: 294,634

[22] Filed: Aug. 23, 1994

Related U.S. Application Data

[63] Continuation-in-part of Ser. No. 254,133, Jun. 6, 1994.

[51] Int. Cl.⁶ ................................................ A61M 25/16
[52] U.S. Cl. ........................................ 604/282; 604/280
[58] Field of Search ................................. 604/282, 281, 604/280

[56] References Cited

U.S. PATENT DOCUMENTS

| | | |
|---|---|---|
| 561,059 | 5/1896 | Mitchell et al. . |
| 1,248,492 | 12/1917 | Hill ............................ 604/165 |
| 3,225,762 | 12/1965 | Guttman ..................... 128/214 |
| 3,352,306 | 11/1967 | Hirsch ........................ 128/214.4 |
| 3,454,006 | 7/1969 | Langdon .................... 604/164 |
| 3,463,152 | 8/1969 | Sorenson .................... 128/214.4 |
| 3,630,195 | 12/1971 | Santomieri .................. 128/133 |
| 3,834,380 | 9/1974 | Boyd ........................... 128/133 |
| 4,194,504 | 3/1980 | Harms et al. ................ 128/214.4 |
| 4,249,541 | 2/1981 | Pratt ........................... 128/753 |
| 4,270,835 | 6/1981 | Bogue et al. ................ 604/44 |
| 4,327,722 | 5/1982 | Groshong et al. .......... 128/214.4 |
| 4,353,369 | 10/1982 | Muetterties ................. 128/214.4 |
| 4,392,856 | 7/1983 | Lichtenstein ................ 604/177 |
| 4,431,426 | 2/1984 | Groshong et al. .......... 604/280 |
| 4,439,583 | 3/1984 | Gould et al. ................ 525/127 |
| 4,525,157 | 6/1985 | Vaillancourt ................ 604/52 |
| 4,529,399 | 7/1985 | Groshong et al. .......... 604/53 |
| 4,549,879 | 10/1985 | Groshong et al. .......... 604/247 |
| 4,559,046 | 12/1985 | Groshong et al ........... 604/282 |
| 4,588,398 | 5/1986 | Daugherty et al. ......... 604/265 |
| 4,627,841 | 12/1986 | Dorr ............................ 604/158 |
| 4,668,225 | 5/1987 | Russo et al. ................ 604/270 |
| 4,671,795 | 6/1987 | Mulchin ...................... 604/281 |
| 4,671,796 | 6/1987 | Groshong et al. .......... 604/247 |
| 4,680,029 | 7/1987 | Ranford et al. ............. 604/280 |
| 4,690,675 | 9/1987 | Katz ............................ 604/177 |
| 4,701,166 | 10/1987 | Groshong et al. .......... 604/247 |
| 4,728,322 | 3/1988 | Walker et al. .............. 604/165 |
| 4,769,016 | 9/1988 | Labianca .................... 604/280 |
| 4,770,655 | 9/1988 | Haber et al. ................ 604/110 |
| 4,772,264 | 9/1988 | Cragg ......................... 604/158 |
| 4,772,276 | 9/1988 | Wiita et al. ................. 604/283 |
| 4,773,901 | 9/1988 | Norton ........................ 604/265 |
| 4,798,597 | 1/1989 | Vaillancourt ................ 604/270 |
| 4,828,549 | 5/1989 | Kvalo ......................... 604/164 |
| 4,846,799 | 7/1989 | Tanaka et al. .............. 604/158 |

(List continued on next page.)

FOREIGN PATENT DOCUMENTS

| | | |
|---|---|---|
| 0247590 | 12/1987 | European Pat. Off. . |
| WO9007349 | 7/1990 | European Pat. Off. . |

OTHER PUBLICATIONS

Landmark Venous Access Device, Menlo Care, Inc., 2 pages (no date).

*Primary Examiner*—Paul J. Hirsch
*Attorney, Agent, or Firm*—Stetina Brunda & Buyan

[57] ABSTRACT

A catheter has an abutment member formed proximate the distal end thereof. The abutment member abuts a complimentary abutment surface formed upon an introducer so as to prevent collapsing of the catheter body during the insertion process. The abutment member preferably comprises an annular abutment shoulder, which reduces the diameter of the lumen of the catheter. An opening formed in the catheter body proximate the tip of the catheter facilitates fluid flow through the lumen of the catheter in the event that the reduced diameter portion of the lumen becomes obstructed. The tip of the catheter preferably comprises a rigid material, so as to assure positive locking action of the abutment member of the catheter with the abutment surface of the introducer during the insertion process.

4 Claims, 2 Drawing Sheets

U.S. PATENT DOCUMENTS

| | | | |
|---|---|---|---|
| 4,846,812 | 7/1989 | Walker et al. | 604/264 |
| 4,863,432 | 9/1989 | Kvalo | 604/177 |
| 4,887,998 | 12/1989 | Martin et al. | 604/110 |
| 4,895,564 | 1/1990 | Farrell | 604/164 |
| 4,898,591 | 2/1990 | Jang et al. | 604/282 |
| 4,911,691 | 3/1990 | Aniuk et al. | 604/164 |
| 4,917,671 | 4/1990 | Chang | 604/168 |
| 4,927,415 | 5/1990 | Brodsky | 604/164 |
| 4,944,728 | 7/1990 | Carrell et al. | 604/164 |
| 4,950,252 | 8/1990 | Luther et al. | 604/198 |
| 4,955,863 | 9/1990 | Walker et al. | 604/165 |
| 4,976,704 | 12/1990 | McLees | 604/265 |
| 4,986,814 | 1/1991 | Burney et al. | 604/281 |
| 4,994,046 | 2/1991 | Wesson et al. | 604/198 |
| 4,998,919 | 3/1991 | Schnepp-Pesch | 604/164 |
| 5,002,533 | 3/1991 | Jullien | 604/110 |
| 5,026,353 | 6/1991 | Bartman | 604/192 |
| 5,034,005 | 7/1991 | Appling | 604/280 |
| 5,037,402 | 8/1991 | Bartman | 604/198 |
| 5,047,018 | 9/1991 | Gay et al. | 604/165 |
| 5,112,312 | 5/1992 | Luther | 604/177 |
| 5,120,317 | 6/1992 | Luther | 604/158 |
| 5,135,502 | 8/1992 | Koenig, Jr. | 604/164 |
| 5,147,332 | 9/1992 | Moorehead | 604/247 |
| 5,205,829 | 4/1993 | Lituchy | 604/164 |
| 5,273,540 | 12/1993 | Luther et al. | 604/110 |
| 5,401,257 | 3/1995 | Chevalier, Jr. et al. | 604/280 |
| 5,423,764 | 6/1995 | Fry | 604/280 |

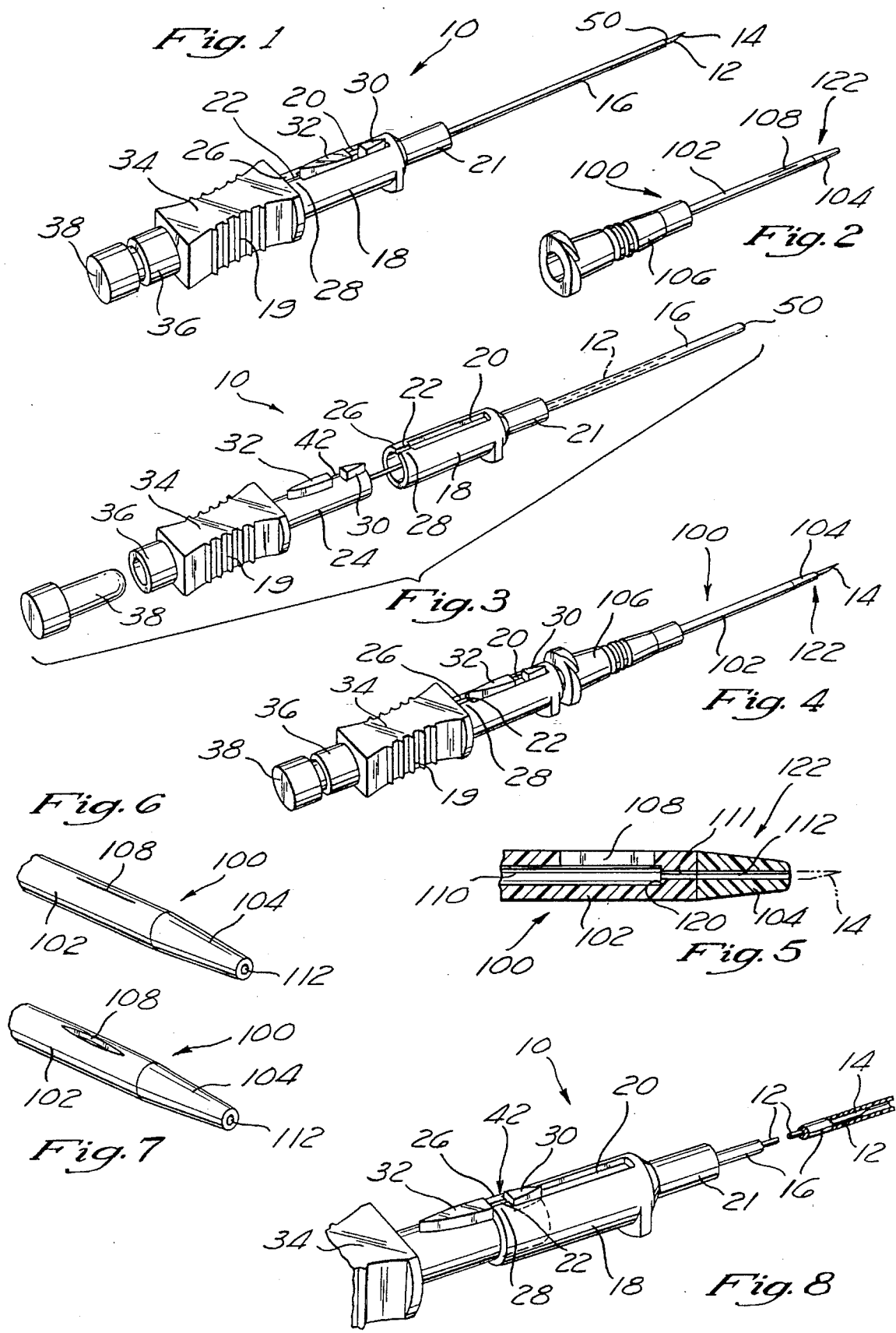

OVER-THE-NEEDLE CATHETER

RELATED APPLICATIONS

This patent application is a continuation in part patent application of U.S. application Ser. No. 08/254,133, filed on Jun. 6, 1994 and entitled Improved Over-The-Needle Catheter, the contents of which are hereby incorporated by reference.

FIELD OF THE INVENTION

The present invention relates generally to medical insertion devices and more particularly to an improved over-the-needle catheter for infusing and withdrawing fluids in the performance of therapeutic and diagnostic medical procedures. The catheter has an abutment member formed near the distal end thereof so as to engage a distal portion of an introducer in a manner which prevents collapsing of the catheter body during the insertion process. A slot formed proximate the catheter tip assures continued fluid flow in the event that the tip becomes obstructed.

BACKGROUND OF THE INVENTION

Vascular/venous access devices for introducing catheters into a patient's vascular system are well known. The simplest of such devices comprises a through-the-needle catheter which is inserted via a cannula. The cannula generally comprises a metal needle inserted into the patient's vein through which the catheter is subsequently introduced.

A common problem associated with the use of such prior art through-the-needle catheter systems arises in removing the cannula after the catheter has been introduced into the vein. Since the cannula is typically comprised of a rigid metal needle, it is desirable to remove the cannula from the patient's vein after insertion of the catheter to prevent trauma to the vein caused by the cannula's rigid structure and/or sharp tip. However, once the catheter has been inserted into the vein, the cannula can typically only be removed by retracting the same upwardly along the catheter, thereby undesirably exposing the patient as well as administering personnel to accidental contact with the cannula.

In recognizing the problems associated with through-the-needle catheter systems, over-the-needle catheter systems have become widely utilized for venous/vascular access applications. In such over-the-needle catheter systems, a thin catheter having a hub at its proximal end is placed over a rigid cannula, such as a needle, whereby the cannula as well as the catheter are simultaneously inserted into the vein of a patient. Once the cannula and catheter have been introduced into the vein, the cannula may be withdrawn from the interior of the catheter, leaving the catheter disposed within the patient's vein. Subsequently, required administration line communication can be effectuated with the catheter by interconnection with its hub mounted to the proximal end of the catheter.

One problem commonly associated with such contemporary over-the-needle catheters is that they tend to travel axially away from the tip of the needle and thus collapse during the insertion process. The skin and tissue tend to push the distal tip of the catheter body backward, or proximally resisting the introduction of the distal end of the catheter therethrough. The catheter body thus wrinkles in an accordion or bellows-like manner over the needle as the distal end of the catheter travels backward toward the proximal end thereof while the needle of the introducer is urged through the skin and tissue.

Thus, such contemporary over-the-needle catheters must possess sufficient rigidity to prevent the same from traveling axially backward relative to the cannula upon which they are disposed during the insertion process. Because of the need for such rigidity, contemporary over-the-needle catheters are incapable of being inserted through the length of a vein or artery without causing substantial trauma and/or puncture thereto.

Another problem associated with such over-the-needle catheters is that the opening in the distal tip thereof occasionally becomes either completely or partially obstructed, thus mitigating fluid flow through the catheter. Various types of particulate matter may facilitate such plugging of the opening in the distal tip of the catheter. For example, small pieces of tissue, i.e., skin, fatty tissue, vascular tissue, etc., may plug the tip of the catheter.

As such, although contemporary over-the-needle catheters have proven generally suitable for their intended purposes, they possess inherent deficiencies which detract from their overall effectiveness and reliability. Moreover, it is desirable to provide an improved over-the-needle catheter which is not subject to becoming compressed during the insertion process and yet which is not so rigid as to cause trauma to blood vessels and the like. It is also desirable to provide an improved over-the-needle catheter which will continue to allow fluid flow therethrough in the event that the opening in the distal end thereof becomes plugged.

SUMMARY OF THE INVENTION

The present invention specifically addresses and alleviates the above-mentioned deficiencies associated with the prior art. More particularly, the present invention comprises a catheter comprising an elongate flexible body having a distal end with a tip formed thereon. The flexible body is preferably formed of a material having sufficient flexibility and resiliency to facilitate movement of the catheter through a substantial length of blood vein, artery, or the like without causing substantial trauma thereto. A common bore or lumen is formed through the catheter body and tip. An abutment member, preferably an annularly configured abutment shoulder, engages a corresponding portion of an introducer utilized with the catheter in a manner which maintains tension along the inserted portion of the catheter body, thereby preventing collapsing of the catheter body during the insertion process. The abutment member is preferably formed within the lumen of the catheter proximate the distal end of the catheter body. Thus, the abutment member engages the introducer in a manner which prevents proximal movement of the catheter tip along the cannula of the introducer in a manner which facilitates collapsing of the catheter.

Preferably, the abutment shoulder is formed at the distal end of the catheter body within the lumen thereof and just proximal of the tip thereof, such that the abutment shoulder abuts the distal-most surface of a needle guard portion of a safety introducer in a manner which prevents the catheter body from collapsing during the insertion process. The abutment shoulder of the catheter thus engages the distal tip of the needle guard and effectively locks the distal tip of the catheter in position during the insertion process, such that the catheter cannot move proximally and thereby collapse.

A first opening to the lumen is formed at the tip and a second opening to the lumen is formed in the catheter body proximate the tip such that when the tip is disposed within a desired anatomical structure, both the first and second openings are typically disposed within the same anatomical structure. The second opening facilitates fluid flow through the lumen of the catheter in the event that fluid flow through the first opening is mitigated.

The formation of such an abutment shoulder inherently necessitates that a region of reduced diameter be formed in the lumen of the catheter body. Such a region of reduced diameter exacerbates the problem of the catheter becoming obstructed since smaller objects can then plug the lumen. Thus, because of the reduced diameter of the catheter bore at the distal end thereof, the second opening is provided so as to assure continued fluid flow through the bore of the catheter in the event that the tip should become obstructed.

The second opening preferably comprises a slit having a closed configuration wherein fluid flow therethrough is inhibited and also having an open configuration wherein fluid flow therethrough is facilitated. The slit is preferably less than approximately 0.25 inch from the first opening and is preferably configured to facilitate fluid flow therethrough when a pressure differential of at least approximately 2 psi exists across the second opening. The slit is preferably between approximately 0.1 inch and approximately 0.50 inch in length, preferably approximately 0.25 inch in length.

The tip of the catheter preferably comprises a harder material than the body thereof. The hard tip resists collapsing, in and of itself, and further increases the reliability of the abutment member. The abutment member, which is preferably formed at an annular abutment shoulder, is substantially reinforced by the more rigid tip. In the preferred embodiment of the present invention, the tip comprises a lumen having a region of reduced diameter sized such that the needle of the introducer easily fits therethrough, however, the needle guard thereof does not fit therethrough. Thus, the rigid tip is prevented from sliding over the needle guard such that the tip acts as a backup or redundant abutment for the annularly configured abutment surface. Thus, if the abutment shoulder should somehow be forced over the introducer's needle guard, then the reduced diameter of the lumen within the tip would inhibit any further distal movement of the tip and thus still prevent collapsing of the catheter.

The tip may optionally comprise a metal. The metal may either be substantially solid or may comprise metal particles, flakes, chips, grounds, etc. so as to render the tip radiopaque. The use of such a hard tip may further facilitate or exacerbate obstruction of the tip since softer tips more readily deform so as to dislodge obstructions. In this regard, the second opening provides even further benefit.

Optionally, the tip comprises a material which softens upon contact with moisture or upon reaching a temperature approximately equal to body temperature. Thus, the tip is sufficiently rigid as to facilitate insertion thereof, and then softens subsequent to insertion so as to facilitate movement through vessels without causing trauma to the walls thereof.

Two examples of catheters having a tip which softens after insertion thereof are disclosed in U.S. Pat. No. 5,112,312, issued on May 12, 1992 to Luther, and entitled VASCULAR/VENOUS ACCESS DEVICE AND METHOD OF UTILIZING AND FORMING THE SAME and in U.S. Pat. No. 5,120,317, issued on Jun. 9, 1992 to Luther, and entitled VASCULAR/VENOUS ACCESS DEVICE AND METHOD OF UTILIZING AND FORMING THE SAME, the contents of both of which are hereby incorporated by reference.

The slit may additionally be utilized to facilitate insertion of the catheter by passing a needle or stylet therethrough such that the sharp tip of the needle or stylet protrudes from the first opening formed in the tip. The needle or stylet thus does not need to be disposed within the entire length of the catheter lumen, thereby facilitating the use of catheters having an extended length. This procedure is taught in U.S. Pat. Nos. 5,112,312 and 5,120,317, the contents of both of which were incorporated by reference above.

The introducer with which the improved over-the-needle catheter of the present invention is utilized preferably comprises a tubular needle guard which covers the needle thereof and extends to a position proximate the sharp tip of the needle. The distal most portion of the needle guard thus defines an abutment surface suitable for contacting the abutment member of the catheter and thereby maintaining the position of the distal end of the catheter during the insertion process so as to prevent collapsing of the catheter body. Those skilled in the art will recognize various other, alternative, configurations of the introducer likewise suitable for providing such an abutment surface. For example, an abutment shoulder, bump, annular surface, or other such feature could be formed upon the distal end of the introducer needle, proximately tip thereof, so as to similarly engage the abutment member of the catheter. Thus, the use of such an introducer having a needle guard is by way of illustration only, and not by way of limitation.

The present invention provides an improved over-the-needle catheter, the distal end of which engages the introducer in a manner which prevents collapsing of the catheter body during the insertion process and also having a second opening formed in the distal end thereof so as to assure continued fluid flow through the lumen of the catheter should obstruction of the tip occur.

These, as well as other, advantages of the present invention will be more apparent from the following description and drawings. It is understood that changes in the specific structure shown and described may be made within the scope of the claims without departing from the spirit of the invention.

BRIEF DESCRIPTION OF THE DRAWINGS

FIG. 1 is a perspective view of an exemplary introducer for facilitating insertion of the improved over-the-needle catheter of the present invention;

FIG. 2 is an enlarged perspective view of the improved over-the-needle catheter of the present invention;

FIG. 3 is an exploded perspective view of the introducer of FIG. 1;

FIG. 4 is a perspective view of the introducer of FIGS. 1 and 3 having the improved over-the-needle catheter of the present invention disposed over the needle thereof so as to facilitate insertion of the catheter;

FIG. 5 is an enlarged cross-sectional view of the distal end of the improved over-the-needle catheter of the present invention showing the tip, first opening formed within the tip, and the second opening formed in the catheter body proximate the tip;

FIG. 6 is a perspective view of the distal end of the improved over-the-needle catheter of the present invention showing the second opening in a closed configuration thereof;

FIG. 7 is a perspective view of the distal end of the improved over-the-needle catheter of the present invention showing the second opening in an open configuration thereof;

FIG. 8 is an enlarged perspective view of the introducer of FIGS. 1, 3, and 4 showing the needle guard thereof in its deployed or extended position so as to cover the sharp tip of the needle, thereby rendering it harmless;

DETAILED DESCRIPTION OF THE PREFERRED EMBODIMENT

Figure 9:
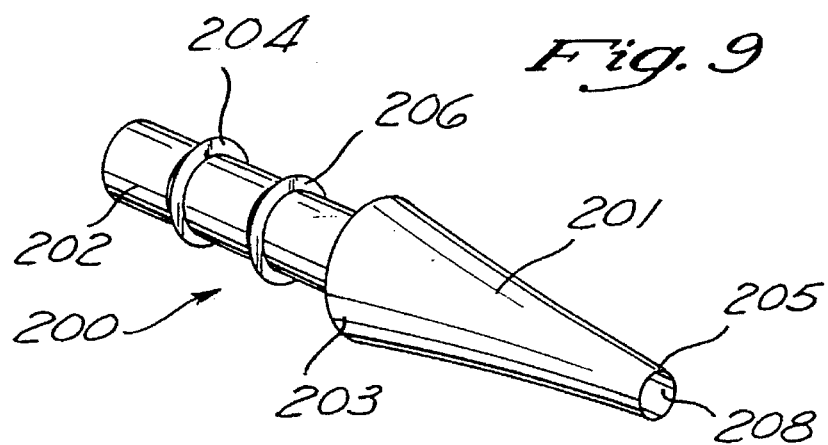
FIG. 9 is a perspective view of a rigid tip insert for the improved over-the-needle catheter of the present invention.

The detailed description set forth below in connection with the appended drawings is intended as a description of the presently preferred embodiment of the invention, and is not intended to represent the only form in which the present invention may be constructed or utilized. The description sets forth the functions and sequence of steps for constructing and operating the invention in connection with the illustrated embodiment. It is to be understood, however, that the same or equivalent functions and sequences may be accomplished by different embodiments that are also intended to be encompassed within the spirit and scope of the invention.

The improved over-the-needle catheter of the present invention is illustrated in FIGS. 2, 4–7 and 9–11 which depict a presently preferred embodiment of the invention. FIGS. 1, 3, and 8 depict an introducer for inserting the improved over-the-needle catheter of the present invention into an anatomical structure such as a blood vein or artery.

Referring now to FIGS. 1 and 3, an introducer 10 for use with the present invention is shown without having the improved over-the-needle catheter of the present invention disposed upon the needle 12 thereof. The introducer 10 with which use of the improved over-the-needle catheter of the present invention is illustrated and described in this patent application is a non-stick or safety introducer which utilizes a sheath or guard 16 to cover the sharp tip 14 of the needle 12 thereof after use of the introducer 10. Thus, the safety introducer 10 prevents the inadvertent and potentially dangerous sticking of a person with the needle 12 thereof. This is particularly important in view of the highly contagious and/or fatal nature of such diseases as AIDS and Hepatitis A.

The use of such a safety introducer 10 in this patent application is by way of example only, and not by way of limitation. Those skilled in the art will recognize that the improved over-the-needle catheter of the present invention may likewise be utilized with a variety of different types of introducers. Indeed, the improved over-the-needle catheter of the present invention may optionally be utilized with simple needles and/or stylets. However, the greatest benefits are attained when the improved over-the-needle catheter of the present invention is utilized with an introducer, needle, or stylet having an abutment surface formed thereon which engages the abutment member of the catheter so as to prevent collapsing thereof during the insertion process.

The safety introducer 10 thus comprises a needle 12 having a sharp tip 14. A substantial portion of the length of the needle 12 is covered by the guard 16. The tip 14 of the needle 12 remains exposed, i.e., not covered by the guard 16, so as to facilitate introduction of the needle 12 and catheter through the skin and tissue of a patient and into an anatomical structure, typically a blood vessel, thereof.

With particular reference to FIG. 3, the sheath 16 is formed to a sliding sleeve 18 having a slot 20 formed therein. A cut 22 is formed in-line and continuous with the slot 20 in the sliding sleeve 18 so as to facilitate assembly thereof upon base 24 of the safety introducer 10 and also so as to facilitate actuation thereof after use, as discussed in detail below. First 26 and second 28 detents are formed upon either side of the cut 22. A first wedge 30 is formed upon the base 24, having its pointed end oriented toward the needle 12, and a second, larger wedge 32 is formed in line with the first wedge 30 upon the base 24, having its point oriented away from the needle 12.

The base 24 is formed to a transparent handle 34 which also defines a flash chamber formed therein. A finger hold 19 is preferable formed upon either side of the handle 34. Boss 36 extends from the handle and receives a porous hydrophobic plug 38 which facilitates venting of air from the flash chamber formed within the handle 34 while also preventing undesirable leakage of blood therefrom. A fitting, preferably a male Luer lock 21, is formed upon the distal end of the sliding sleeve 18.

To assemble the safety introducer 10, the sliding sleeve 18 is pushed onto the base 24 such that the needle 12 is received within the guard 16 and the pointed end of the first wedge 30 slides into and forces open the cut 22 in the sliding sleeve 18. By opening the cut 22 in the sliding sleeve 18, the first wedge 30 allows the sliding sleeve 18 to be slid over the base 24 into a position as illustrated in FIGS. 1 and 4, wherein both the first 30 and second 32 wedges are disposed within the slot 20. In this position, the tip 14 of the needle 12 remains exposed so as to facilitate use of the safety introducer 10.

Referring now to FIG. 8, after use of the safety introducer 10, the sliding sleeve 18 thereof is pushed distally, i.e., toward the needle 12. As the sliding sleeve 18 is urged distally, the second wedge 32 forces open the cut 22 so as to allow the first 26 and second 28 detents to ride up over the wedge 32 and then to snap back together into the opening 42 formed between the first 30 and second 32 wedges, thereby locking the guard 16 formed upon the sleeve 18 in an extended or deployed position. When the sliding sleeve 18 is thus locked in its distal position, the tip 14 of the needle 12 is covered and obscured by the guard 16 so as to prevent inadvertent sticking therewith.

Referring now to FIG. 2, the improved over-the-needle catheter 100 of the present invention is illustrated. The catheter comprises a flexible body 102 having a comparatively rigid tip 104 formed upon the distal end thereof. The body 102 is formed to a fitting or hub, preferably a female Luer lock 106. A slit 108 is formed at the distal end of the body 102 of the catheter 100, proximate the tip 104 thereof.

Referring now to FIGS. 4 and 5, the improved over-the-needle catheter 100 is illustrated disposed upon the introducer 10 of FIGS. 1, 3, and 8. The female Luer lock 106 of the improved over-the-needle catheter 100 attaches to the male Luer lock 21 of the introducer 10. When thus installed, the needle guard 16 and needle 12 of the introducer 10 are both disposed within the lumen of the catheter body 102 such that the catheter guard 16 does not extend from the tip 104 of the catheter 100 and the point 14 of the needle 12 does extend therefrom in a manner which facilitates use of the introducer 10 to insert the improved over-the-needle catheter 100 of the present invention into a blood vessel or the like.

When the catheter 100 is so disposed upon the introducer 10, the abutment shoulder (120 of FIG. 5) abuts the distal most surface 50 of the needle guard 16. The diameter of the needle guard 102 is too large to pass through the region of reduced diameter 111 of the catheter body 102 and the region of reduced diameter 112 of the tip 104. Thus, the distal end 122 and tip 104 of the catheter 100 are prevented from moving proximally during the insertion process, thereby preventing collapsing of the catheter body 102. The needle 12 is sized to have a diameter less than that of the region of reduced diameter 111 of the catheter body 102 and the region of reduced diameter 112 of the tip 104 such that the needle 12 extends therethrough and the point 14 of the needle 12 extends from the tip 104 so as to facilitate the insertion process.

With particular reference to FIG. 5, the abutment shoulder 120 is formed at the distal end 122 of the catheter body 102. The abutment shoulder 120 abuts the distal-most surface 50 of the needle guard 16 when the improved over-the-needle catheter 100 of the present invention is installed upon the inserter 10. Thus, the catheter body 102 is prevented from collapsing upon the needle 12 and/or needle guard 16 of the introducer 10 during the insertion process. Rather, the distal end 122 of the catheter 100 is maintained in position proximate the point 14 of the needle 12 during the insertion process.

The slit 108 assures continued fluid communication from the lumen 110 formed within the body 102 of the catheter 100 in the event that the region of reduced diameter 111 of the catheter 100 or the region of reduced diameter 112 tip 104 becomes obstructed. The size of the region of reduced diameter 111 of the catheter body 102 and the region of reduced diameter 112 of the tip 104 increases the probability of obstruction due to the inherently reduced cross-sectional area thereof, thus making these areas more susceptible to plugging. Thus, the slit 108 provides an alternate means for facilitating fluid 12 flow between the lumen 110 of the catheter 100 and the anatomical vessel within which the distal end 122 of the catheter 100 is disposed.

Optionally, a plurality of such slits may be provided so as to further assure continued fluid communication from the lumen 110 to or from the anatomical structure, Indeed, those skilled in the art will recognize that a variety of different numbers and configurations of such openings are likewise suitable.

Referring now to FIG. 6, the slit 108 is illustrated in a closed position wherein fluid communication is provided through the catheter 100 only via the reduced diameter lumen 111 extending through the distal end of the catheter body 102 and the reduced diameter lumen 112 extending through the tip 104 thereof. The slit 108 remains in such a closed position until the pressure within the lumen 110 exceeds the pressure outside the lumen 110 by a predetermined amount, preferably approximately 2 psi, during a fluid infusion process or the pressure outside the lumen exceeds the pressure inside the lumen 110 by a predetermined amount, preferably approximately 2 psi, during a fluid withdrawal process.

It is not uncommon for the opening in the tip of a catheter to become obstructed. This may occur either during the insertion process or thereafter. Clotting blood, tissue fragments, etc. may plug or partially obscure the lumen of a catheter, thereby substantially limiting fluid flow therethrough.

The use of such a slit 108 facilitates fluid flow both into and out of the catheter 100. Thus, whether the catheter is being utilized to introduce fluids into a patient, or to withdraw fluids therefrom, the slit 108 may function to maintain desired flow through the catheter 100 in the event that the tip 104 should become obstructed.

Referring now to FIG. 7, the slit 108 is illustrated in an open configuration wherein fluid communication is provided therethrough from the lumen 110 as would occur if fluids were being either infused or withdrawn via the catheter 100 and one or both of the reduced diameter lumens 111 or 112 should become obstructed or the flow therethrough becomes substantially reduced.

The tip 104 is preferably formed of a harder or more rigid material than the body 102 of the catheter so as to prevent collapsing thereof during the insertion process by maintaining the position of the distal end 122 and tip 104 of the catheter body 102 proximate the point 14 of the needle 12 during the insertion process. The use of such a comparatively rigid tip 104 assures that the tip 104 does not ride up over the distal-most surface 50 of the needle guard 16 during the insertion process, thereby allowing the catheter body 102 to collapse. The tip 104 may optionally be formed of a material which is initially hard and then softens upon contact with moisture in body fluids, such as blood, or which softens upon being heated to approximately body temperature. Thus, the tip 104 remains sufficient rigid to facilitate insertion and then softens so as to mitigate the occurrence of trauma to vascular walls as the catheter 100 is manipulated therein.

The tip 104 preferably comprises a radiopaque material such as metal particles, flakes, granules, chips, etc. Alternatively, the tip may be comprised entirely of metal. Such construction both facilitates introduction of the catheter into a vessel due to the rigidity thereof and provides a radiopaque target for use in radiographic visualization of the insertion process. The use of a metal tip additionally assures that the lumen formed therethrough will not expand so as to allow for the tip to ride up over the distal-most surface 50 of the needle guard 16 so as to allow the catheter body 102 to collapse during the insertion process.

The slit 108 may additionally be utilized to facilitate the insertion of a needle or stylet therethrough. The needle or stylet extends through the lumen of the catheter and on through the tip 104. The point of the needle or stylet thus extends from the tip 104 so as to facilitate insertion of the catheter into an anatomical structure. Thus, the approved over-the-needle catheter of the present invention may be so used with a standard needle or stylet, as desired.

Figure 10:
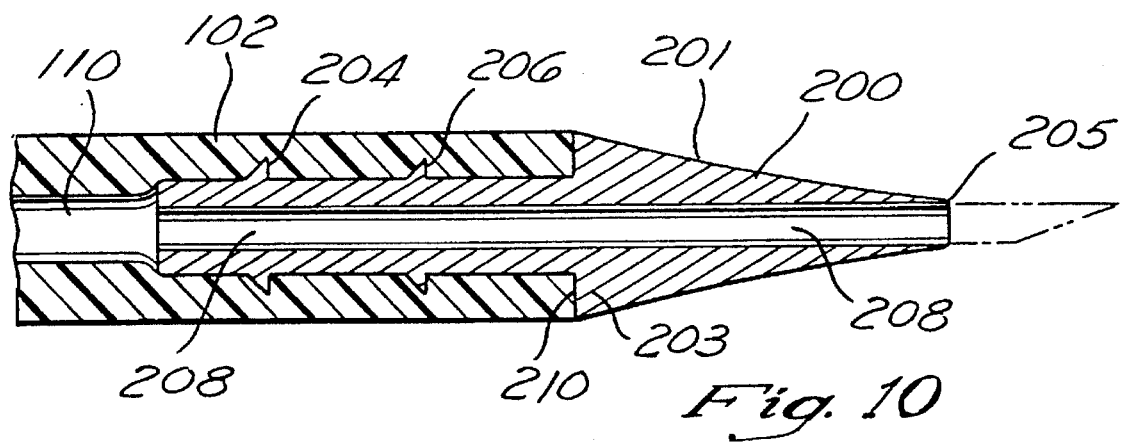
FIG. 10 is a cross-sectional side view of the rigid tip insert of FIG. 9 inserted into the distal end of the catheter body.
Figure 11:
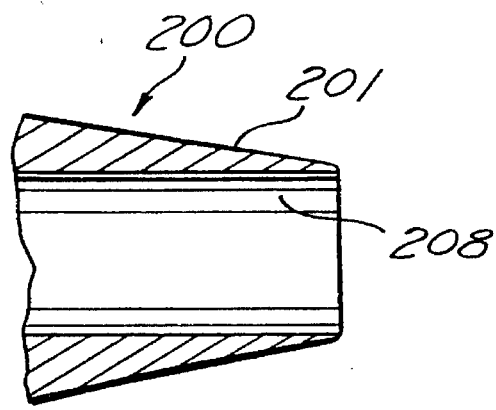
FIG. 11 is an enlarged cross-sectional side view of the distal end of the catheter tip insert of FIGS. 9 and 10.

Referring now to FIGS. 9–11, a hard tip insert 200 is preferably disposed at the distal end of the catheter body 102. The insert 200 tends to prevent compaction or axial collapsing of the catheter body 102 during the insertion process. The insert 200 is formed of a hard material, preferably metal, such that it is more readily inserted through skin and tissue while resisting deformation. Those skilled in the art will recognize a variety of other materials, e.g., plastic, etc., may likewise be utilized..

The hard catheter tip 200 comprises a fresto-conical member 201 having a base 203 which has a diameter approximately equal to the outer diameter of the catheter and having a tip 205 having a diameter proximately equal to the inner diameter of the catheter. A bore 208 extends through the base and has a diameter approximately equal to that of the tip 205.

A shaft 202 extends from the proximal end of the fresto-conical member 201 and preferably has an outer diameter greater than the inner diameter of the catheter body 102 and less than the outer diameter thereof. The bore 208 extends axially through the shaft 202, as well as the fresto-conical member 201. A plurality, preferably two, of annularly configured barbs 204 and 206 are formed about the shaft 202 and anchor the shaft 202 within the bore of the catheter body 102.

The hard tip insert 200 is assembled to the distal end of the catheter body 102 by simply pushing the shaft 202 of the insert 200 into the lumen 110 of the catheter body 102 until the distal end of the catheter body 102 abuts the shoulder 210 of the insert 200. Once so assembled, the barbs 204 and 206 engage the lumen 110 and prevent undesirable removal of the insert 200 from the catheter body 102. Optionally, an adhesive or thermal bonding may be utilized to further secure the insert 200 to the catheter body 102.

Thus, in use, the method for utilizing the improved over-the-needle catheter of the present invention comprises supporting a distal end of the catheter in a manner which prevents collapsing thereof and then urging the distal end of the catheter into the anatomical structure. Supporting of the distal end of the catheter end is typically discontinued after urging the distal end of the catheter into the anatomical structure.

More particularly, the improved over-the-needle catheter is utilized by first inserting the catheter 100 upon the needle 12 and needle guard 16 of the introducer 10 having the needle 12 in the deployed position thereof, i.e., the needle guard 16 retracted so as to expose the point 14 of the needle 12. The point 14 is then urged into the desired anatomical structure, with the tip 104 of the catheter 100 moving along therewith. The catheter 100 cannot collapse since the tip 104 is prevented from moving proximally by the abutment shoulder 120 which contacts the distal end 50 of the needle guard 16. When the tip 104 of the catheter 100 is positioned within the anatomical structure, as desired, the female Luer lock 106 is held firmly in place as the introducer 10 is withdrawn from the catheter 100.

Prior to completely withdrawing the needle 12 from the catheter 100, the needle guard 16 is deployed so as to cover the point 14 of the needle 12, thereby preventing accidental needle sticks. Deployment of the needle guard 16 is preferably accomplished by continuing to withdraw the introducer 10 from the catheter 100 by retracting the handle 34 thereof while maintaining stationary the sliding sleeve 18 such that the cut 22 rides up over the second wedge 32 and the detents 26 and 28 become captured within the opening 42 formed between the first 30 and second 32 wedges, thereby locking the needle guard 16 in the deployed position. Such procedure assures that the needle guard 16 is properly deployed prior to the point 14 of the needle 12 exiting the catheter 100, at which time it would otherwise become a hazard.

It is understood that the exemplary over-the-needle catheter described herein and shown in the drawings represents only a presently preferred embodiment of the invention. Indeed, various modifications and additions may be made to such embodiment without departing from the spirit and scope of the invention. For example, the length of the catheter may be increased substantially to facilitate its use in applications requiring that the tip of the catheter be manipulated through an extended length of the vascular system. Also, various numbers of slits may be formed within the body of the catheter so as to facilitate fluid flow in the event that the tip 112 should become obstructed and/or to facilitate the use of an introducer inserted therethrough, particularly in the event that a comparatively long catheter is utilized. Thus, these and other modifications and additions may be obvious to those skilled in the art and may be implemented to adapt the present invention for use in a variety of different applications.

What is claimed is:

1. An over the needle catheter insertable into an anatomical structure utilizing an introducer, said catheter comprising:

a) an elongate flexible catheter body having a distal end;
    b) an abutment member formed proximate the distal end of said catheter body so as to abut a portion of the introducer to prevent the catheter body from collapsing during insertion of the catheter body;
    c) a catheter tip formed of a more rigid material than said catheter body for mitigating collapsing of the catheter body, said catheter body having an inner diameter and an outer diameter, said catheter tip comprising:
        i) a generally frusto-conical member comprising:
            (A) a base having a diameter approximate to the outer diameter of the catheter body;
            (B) a bore having a diameter approximate to the inner diameter of the catheter body;
            (C) a tip having a diameter approximate the diameter of said bore;
        ii) a shaft extending from the base of said frusto-conical member and co-axial therewith, said shaft having a diameter greater than the inner diameter of the catheter and less than the outer diameter thereof, said shaft having a bore extending co-linear to the bore of said frusto-conical member;
        iii) at least one barb formed upon said shaft to anchor said shaft to said catheter; and
    d) wherein said abutment member and said catheter tip cooperate to facilitate insertion of the catheter body into an anatomical structure in a manner which inhibits collapsing of the catheter body.

2. The catheter as recited in claim 1 wherein said catheter tip comprises a radiopaque material.

3. The catheter as recited in claim 1 wherein said generally frusto-conical member, said shaft, and said barb(s) are formed of a common piece of metal.

4. The catheter as recited in claim 1 wherein said barb(s) comprise annularly configured barb(s) which substantially encircle said shaft.

* * * * *